United States Patent [19]

Hammond et al.

[11] Patent Number: 5,792,389
[45] Date of Patent: Aug. 11, 1998

[54] WATER SOLUBLE LASER DYES

[75] Inventors: Peter R. Hammond, Livermore, Calif.; James F. Feeman, Wyomissing, Pa.; George F. Field, Santa Ana, Calif.

[73] Assignee: United States of America, Washington, D.C.

[21] Appl. No.: 141,752

[22] Filed: Oct. 27, 1993

[51] Int. Cl.$^6$ .......................... F21V 9/00; C07D 265/34; C07D 311/78
[52] U.S. Cl. .................. 252/582; 252/587; 252/589; 544/99; 544/102; 544/103; 544/104; 549/382; 549/383; 549/390; 549/394
[58] Field of Search ................... 544/99, 102, 103, 544/104; 549/382, 383, 390, 394; 252/582, 587, 589

[56] References Cited

U.S. PATENT DOCUMENTS

| | | | |
|---|---|---|---|
| T856,047 | 11/1968 | Wallace et al. | 544/103 |
| 3,681,347 | 8/1972 | Herz et al. | 544/103 |
| 3,772,335 | 11/1973 | Meininger et al. | 549/394 |
| 3,956,300 | 5/1976 | Austin et al. | 549/394 |
| 4,256,882 | 3/1981 | Friedrich et al. | 549/394 |
| 4,362,873 | 12/1982 | Belfort | 544/103 |
| 4,386,216 | 5/1983 | Locatell, Jr. et al. | 549/394 |
| 4,622,395 | 11/1986 | Bellus et al. | 544/103 |
| 5,149,807 | 9/1992 | Hammond et al. | 544/99 |

FOREIGN PATENT DOCUMENTS

WO 93/10189  5/1993  Germany.

*Primary Examiner*—Philip Tucker
*Attorney, Agent, or Firm*—Townsend and Townsend and Crew LLP

[57] ABSTRACT

Novel water soluble dyes of the formula I are provided

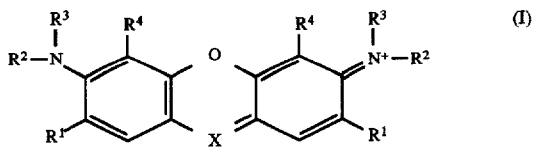

wherein $R^1$ and $R^4$ are alkyl of 1 to 4 carbon atoms or hydrogen; or $R^1$-$R^2$ or $R^2$-$R^4$ form part of aliphatic heterocyclic rings; $R^2$ is hydrogen or joined with $R^1$ or $R^4$ as described above; $R^3$ is —$(CH_2)_m$—$SO_3^-$, where m is 1 to 6; X is N, CH or

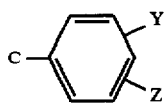

where Y is 2 —$SO_3^-$; Z is 3, 4, 5 or 6 —$SO_3^-$. The novel dyes are particularly useful as the active media in water solution dye lasers.

5 Claims, No Drawings

WATER SOLUBLE LASER DYES

The United States Government has rights in this invention pursuant to Contract No. W-7405-ENG-48 between the United States Department of Energy and The University of California for the operation of Lawrence Livermore National Laboratory.

BACKGROUND OF THE INVENTION

The present invention relates to novel water soluble dyes, and more specifically to sulfonated rhodamine, pyronin and oxazine dyes having monosulfonation on each of the N-alkyl side chains and, where appropriate, having disulfonation on the pendant phenyl group. These dyes lase efficiently in water and are useful in laser applications, as water tracers, fluorescent signs, recreational equipment, fluorescent tags in diagnostic methods, and as well as in other products where fluorescent materials may be required.

One of the uses of fluorescent dyes is in dye lasers. For example, dyes having such use in laser applications are disclosed in U.S. Pat. Nos. 3,932,415 and 4,005,092. Useful dyes for the laser tuning range of 540 to 560 nm and/or 560 to 610 nm require the use of large organic molecules (molecular weight of approximately 500). However, since large organic molecules are insoluble or relatively insoluble in water, heretofore dye lasers have required organic solvent systems, which increase costs because of the safety precautions required due to flammability, volatility and, in some cases, corrosivity and toxicity. Water also has superior optical properties as a laser medium—a small change of its refractive index with temperature and a high thermal capacity.

Furthermore, any attempted use of large organic molecules in aqueous systems causes aggregation, quenching, spectral changes and dimerization of dyes (K. L. Arvan and N. E. Zaitseva, "Influence of solvent on the aggregation of organic dyes," *Optics and Spectroscopy, Engl. Trans.* 1961, 10, 137; J. E. Selwyn and J. I. Steinfeld, "Aggregation equilibria of xanthene dyes," *J. Phys, Chem.*, 1972, 76, 762; F. L. Arbeloa, P. R. Ojeda and I. L. Arbeloa, "Dimerisation and trimerisation of rhodamine 6G in aqueous solution," *J. Chem. Soc., Faraday Trans.* II, 1988, 84, 1093), which are sufficient to inhibit flashlamp-pumped laser operation. Water-mixed solvents, additives and water/micelle systems have problems of long term reliability, stability and performance. U.S. Pat. No. 4,100,509 teaches a laser dye which is stated to be useful in water as a solvent, but shows the use of a cationic surface active substance in the aqueous solution.

It would thus be desirable to have organic dyes which meet the needs of a dye laser but yet which have a high degree of solubility in water or substantially aqueous systems without the need for solubilizing additives.

SUMMARY OF THE INVENTION

In order to achieve this goal, we have found that dye structure may be synthetically modified in such a way as to confer marked water solubility while retaining laser efficiency. Among the three main classes of dyes, the cyanines (from which rhodamines, pyronins and oxazines may be considered derived) are already ionic, and because they can take advantage of the high dielectric constant offer the best prospect for such manipulation. In addition, substituents containing solubilizing groups such as the sulfonate anion, the carboxylate anion, and the substituted tetraalkylammonium cation can be incorporated into the dye structure. For example, solubilizing groups can be attached to the chromophore nitrogens as ethanesulfonate (from chloroethanesulfonic acid), propanesulfonate (from 1,3-propanesultone) (R. F. Fischer, "Propanesultone," *Ind. Eng. Chem.*, 1964, 56, 41; D. W. Roberts and D. L. Williams, "Sultone Chemistry," *Tetrahedron* 1987, 43, 1027) and butanesulfonate (from 1,4-butanesultone) (D. W. Heseltine and L. G. S. Brooker, "Tricarbocyanine infrared-absorbing dyes," U.S. Pat. No. 2,895,955) to enhance water solubility.

Thus, the present invention is directed to a class of water soluble dyes which are particularly useful in laser applications, and provides a family of novel water soluble dyes having monosulfonation on each of the N-alkyl side chains and, in some cases, having disulfonation on the pendant phenyl group.

These novel water soluble dyes are of the following formula I:

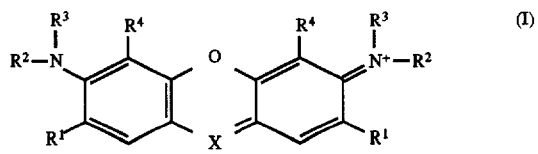

wherein $R^1$ and $R^4$ are alkyl of 1 to 4 carbon atoms or hydrogen; or $R^1$-$R^2$ or $R^2$-$R^4$ form part of aliphatic heterocyclic rings;

$R^2$ is hydrogen or joined with $R^1$ or $R^4$ as described above;

$R^3$ is —$(CH_2)_m$—$SO_3^-$, where m is 1 to 6;

X is N, —CH or

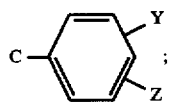

Y is 2 —$SO_3^-$; and

Z is 3, 4, 5 or 6 —$SO_3^-$.

Additional objects, advantages and novel features of the present invention will be set forth in part in the following description.

DETAILED DESCRIPTION OF THE INVENTION

The following description of the preferred embodiments of the present invention is presented for the purposes of illustration and description. It is not intended to be exhaustive or to limit the invention to the precise forms disclosed and obviously many modifications and variations are possible in light of the teachings herein. The particular embodiments described below were chosen and described in order to best explain the principles of the invention and their practical application, to thereby enable others skilled in the art to best utilize the invention in various embodiments and with various modifications as are suited to the particular use contemplated.

The present invention is directed to water soluble dyes of the following formula I:

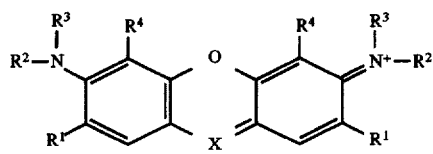 (I)

wherein $R^1$ and $R^4$ are alkyl of 1 to 4 carbon atoms or hydrogen; or $R^1$-$R^2$ or $R^2$-$R^4$ form part of aliphatic heterocyclic rings;

$R^2$ is hydrogen or joined with $R^1$ or $R^4$ as described above;

$R^3$ is —$(CH_2)_m$—$SO_3^-$, where m is 1 to 6;

X is N, CH or

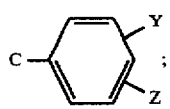

Y is 2 —$SO_3^-$; and

Z is 3, 4, 5 or 6 —$SO_3^-$.

In the above formula I the substituents $R^1$ and $R^4$ may be alkyl of 1 to 4 carbon atoms, including linear as well as branched alkyl groups such as propyl, isopropyl, isobutyl, n-butyl, sec-butyl, ethyl and methyl.

In the variation of formula I wherein $R^1$-$R^2$ form part of heterocyclic rings, these rings may contain a total of 4 to 7 ring atoms, preferably 6 ring atoms, i.e., wherein $R^1$-$R^2$ is —$(CH_2)_3$—, and 5 ring atoms, i.e., wherein $R^1$-$R^2$ is —$(CH_2)_2$—.

A preferred subclass of compounds of the formula I are those wherein X contains benzene-2,4-disulfonate. Preferred compounds within this subclass include those wherein $R^1$-$R^2$ is —$(CH_2)_3$—, wherein $R^1$-$R^2$ is —$(CH_2)_2$—, or wherein $R^1$ or $R^4$ is alkyl and $R^2$ is hydrogen, as illustrated in formula IA, IB, IC, ID respectively.

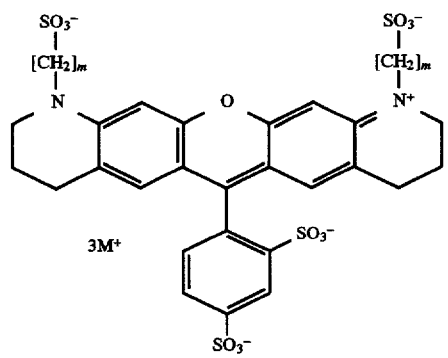 (IA)

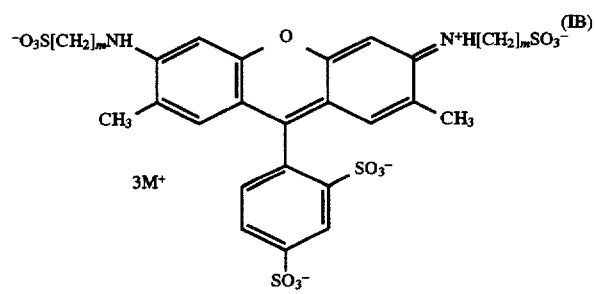 (IB)

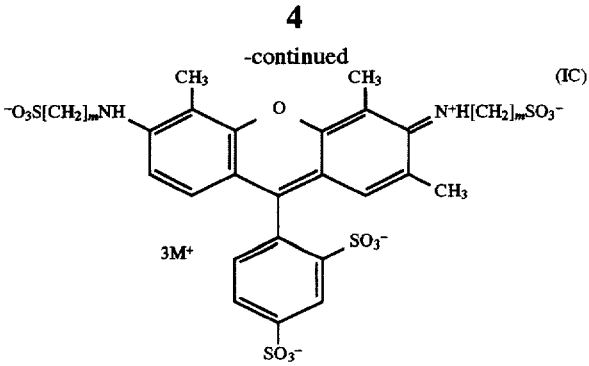 (IC)

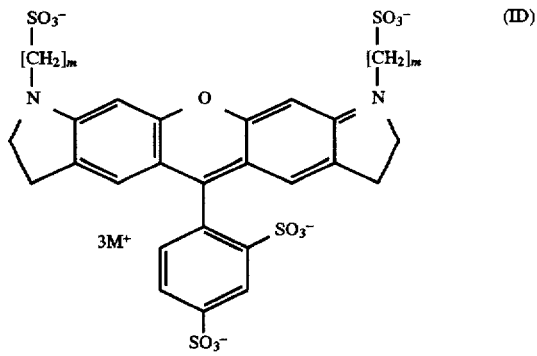 (ID)

Particularly preferred compounds of the formula IA are those wherein $R^3$ is —$(CH_2)_m$—$SO^-_3$, where m is either 3 or 2. Particularly preferred compounds of the formula IB are those wherein m is 3 or 2 and $R^1$ is methyl. Particularly preferred compounds of the formula ID are those wherein m is 3 or 2.

A second preferred subclass of Formula I compounds are those wherein X is CH as illustrated in formula IE. Particularly preferred compounds are those wherein $R^1$-$R^2$ is —$(CH_2)_3$—, $R^3$ is —$(CH_2)_m$—$SO^-_3$, where m is 2.

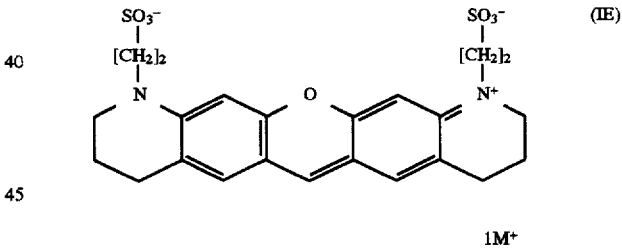 (IE)

A third preferred subclass of formula I compounds are those wherein X is N. Particularly preferred compounds of this formula are those wherein $R^1$-$R^2$ is —$(CH_2)_3$— and $R^3$ is —$(CH_2)_2$—$SO_3^-$ as illustrated in formula IF.

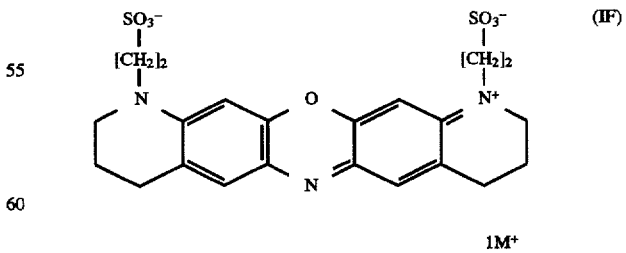 (IF)

The dyes made in accordance with the present invention have an enhanced water solubility to allow water as a solvent in dye lasers. The dyes prepared in the present invention are also useful as water tracers to trace water leaks. Other uses for the dyes according to the present invention include fluorescent coloring agents, fluorescent colors in posters, road safety signs, toys and other products in which fluorescent dyes may be utilized. The dyes according to the present invention may also be useful in chemical and biological research, and therapeutic and diagnostic kits, and in pharmaceutical products where fluorescent markers may be employed. The following examples are presented to help in the better understanding of the present invention and for purposes of illustration. The examples, however, are not to be construed as limiting the invention to the precise form disclosed or to limit the scope of the invention in any manner or means.

Compounds of formula I may be prepared as follows. Referring to scheme 1, compounds of formula I wherein X is benzene-2,4-disulfonate and wherein m is 3 can be produced by the following route.

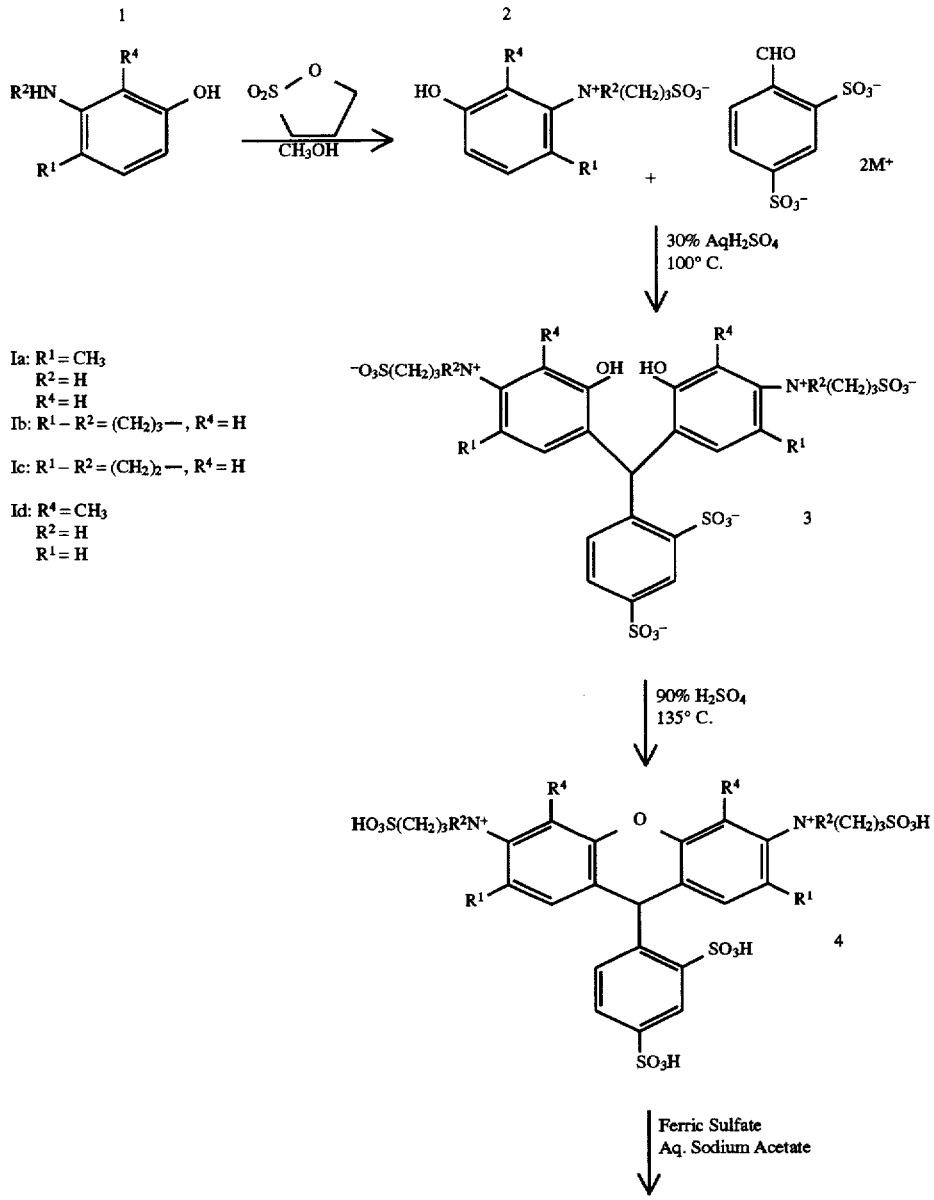

-continued
SCHEME 1

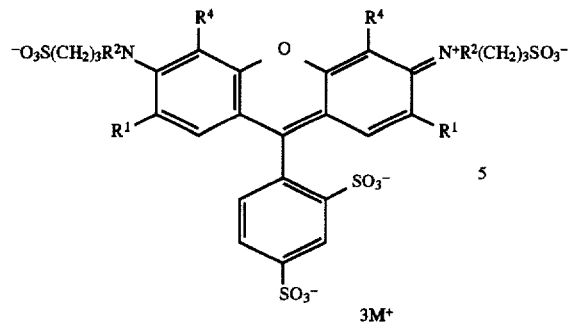

Referring to scheme 1, aminophenols had previously been successfully condensed with 1,3-propane sultone in n-butanol (I. Zeid and I. Ismail, "Synthesis of N-substituted aminosulfonic acids," *Liebigs Ann. Chem.*, 1974, 667). For this invention other solvents were superior, particularly methanol, which gave clean products, although yields (50–55%) were lower than the stated 80%. Good quality starting aminophenols appeared to be necessary, namely 3-amino-4-methylphenol 1a, 7-hydroxyl-1,2,3,4-tetrahydroquinoline 1b, or 6-hydroxyindoline 1c. The aminophenol propane sulfonates 2 were condensed with recrystallized benzaldehyde 2,4-disulfonic acid sodium salt by combining 2 to 2.1 equivalents with 1 equivalent of the benzaldehyde in 30% sulfuric acid at 100°–110° C. to form the leuco acid 3. Ring closure (pyronization) was carried out in about five times the weight of 90% sulfuric acid by heating to 135° C. and holding for two hours to form 4. The sulfonated dye 5 is produced through the oxidation of 4 with ferric sulfate rather than ferric chloride to avoid iron-complex formation.

Compounds according to formula I wherein X contains benzene-2,4-disulfonate and wherein m is 2 may be produced according to scheme 2.

SCHEME 2

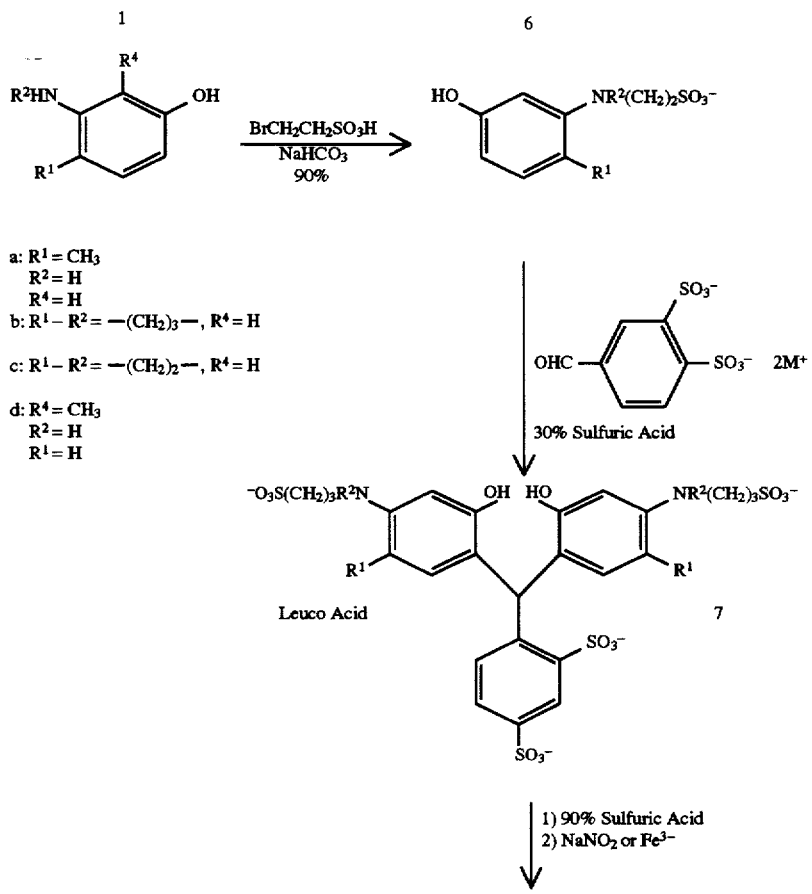

-continued
SCHEME 2

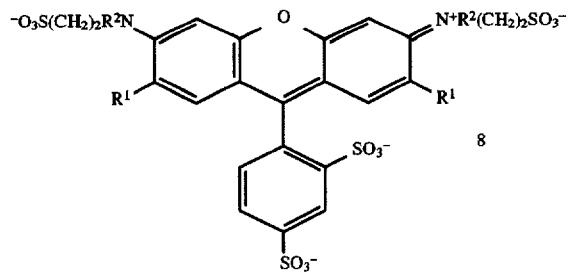

8

Referring to scheme 2, the amino toluene 1a, 7-hydroxy-1,2,3,4-tetrahydroquinoline 1b or 6-hydroxyindoline 1c would be reacted with 2-bromoethanesulfonic acid sodium salt to form the ethanesulfonic acid 6. The resultant 6 would then be further reacted with benzaldehyde-2,4-disulfonic acid to give rise to the leuco acid 7. The same steps involving ring closure and ferric ion oxidation as described in scheme 1 would then be undertaken to prepare sulfonated dye 8. Scheme 2 was successfully performed using starting materials 7-hydroxy-1,2,3,4-tetrahydroquinoline 1b and 6-hydroxyindoline 1c.

Compounds of formula I wherein X is CH (pyronin dye "PQE") or N (oxazine dye "OQE") and wherein $R^1$–$R^2$ was —$(CH_2)_3$— and $R_3$ was —$(CH_2)_2$—$SO_3^-$ were synthesized with good yield.

Preparation of the pyronin dye involves reaction in water/acid of aqueous formaldehyde with 2-N-[7-hydroxy-1,2,3,4-tetrahydroquinolinyl] ethane sulfonic acid 6b, followed by ring closure at 135°–145° C. in 90% $H_2SO_4$, drowning on ice, dilution to about 20% $H_2SO_4$, filtration and wash with water, reslurry in 95% ethanol, oxidation by addition of aqueous sodium nitrite, final filtration and wash with 95% ethanol.

It is important that the starting material be of high purity. To this end synthesis of this intermediate was best accomplished by reaction of 7-hydroxy-1,2,3,4-tetrahydroquinoline (HOTHQ) with 2-bromo-ethane sulfonic acid Na-salt, in water with sodium bicarbonate as the base. Following reaction with 2-bromoethane sodium sulfonate, the crude intermediate 6b was filtered as the sodium salt. This was redissolved in water, acidified, filtered and washed with water and then with ethanol several times. Recrystallization from boiling water with charcoal treatment and filtration, gave highly purified material mp. 296°–302° C.

Oxazine dyes can likewise be synthesized. An example, Oxazine Dye (OQE), was obtained in small amount in pure form. The product obtained directly from condensation with the nitroso intermediate was impure, but could be purified by column chromatography. The purer fractions from this separation, on silica gel using water as elutant, were evaporated to dryness and a portion of this sample recrystallized from 80–85% ethanol.

It will be appreciated that the various reactions described above are preferably utilized; however, other equivalent reactions may be substituted therefor, including reagents which accomplish the same or substantially equivalent results.

EXPERIMENTAL DETAILS

EXAMPLE 1

Preparation of 9-[2,4-disulfophenyl]-3,6-bis(3-sulfopropylamino)-2,7-dimethylxanthylium inner salt, trisodium salt. 5a (1). 3N-[5'-Hydroxy-2'-methylphenyl]-aminopropanesulfonic acid. Propane sultone (58.6 g -97%, 0.4655 mole) was weighed into a 1 l. 3-necked reaction flask fitted with stirrer, condenser, and thermometer. A solution of 3-amino-4-methylphenol (49.3 g, 0.4 mole) dissolved in 400 ml methanol was added with stirring. The clear solution, which clouded upon stirring, was allowed to stir at ambient temperature (35° dropping to 20°) over a weekend. During this time, a large amount of light colored precipitate formed. Thin-layer chromatography on silica gel plates using isopropanol as an eluant was used to follow the reaction. After 66 hours, the crystalline precipitate was filtered and washed on the funnel with about 30 ml methanol. The product was air dried giving 52.8 g (53.8% of theory). Recrystallization of a 4 g sample of this product from 30 ml boiling water, with filtration gave 3 g colorless crystals, m.p. 245°–246° (decomp.) after drying in air, then a vacuum desiccator. It analyzed C 48.91, H 6.22, N 5.71, S 12.64%, whereas $C_{10}H_{15}NO_4S$ requires C 48.97, H 6.16, N 5.71, S 13.07%.

(2). Condensation. In a 250 ml 3-necked round bottom flask were weighed 34.5 g of 96.4% sulfuric acid, 40 g ice and 36.5 g water to make 111 g 30% sulfuric acid. While stirring were added 13.3 g (0.04 mole) dry, recrystallized benzaldehyde 2,4-disulfonic acid sodium salt (the dihydrate) and 25.75 g (0.015 mole) of 3-[N(5'-hydroxy-2'-methylphenyl)]-aminopropanesulfonic acid. The solution was heated to 100° C. and held at approximately this temperature for 16 hours. The acid solution was cooled and transferred to a 400 ml beaker. The sulfuric acid was neutralized at about 70° C. with 30 g calcium hydroxide. After stirring for about one hour, the pH was 10. The calcium sulfate precipitate was filtered and the cake washed four times with 25 ml water each time giving total filtrate of 225 ml. The solution, upon evaporation to near dryness, left 52.1 g of thick reddish colored syrup which solidified upon cooling.

(3). Ring closure. To the above product was added 172 g of 96.4% sulfuric acid and, with heating, a deep yellow solution formed. The amount of sulfuric acid was calculated to produce about five times the weight of starting materials having 90% sulfuric acid content. The acid solution was heated to 135° C. and held for two hours. Ice (317 g) and water (183 g) were added to the cooled sulfuric acid solution to reduce the acid concentration to about 25%.

(4). Oxidation and Purification. The above solution was heated to 90° C. and treated during ten minutes with 30 g of hydrated ferric sulfate (72% min., 0.054 mole). Cooling slowly with stirring for 16 hours to 20° C. gave crystalline precipitate of dye. Filtration and washing of the filter cake with four 25 ml portions of 25% sulfuric acid gave 57.9 g paste.

This was dissolved in 400 ml water and residual sulfuric acid neutralized by adding 6 g calcium hydroxide (pH 1.0). Then, after heating to 50°–60° C., sodium carbonate (16 g)

was added to raise the pH to 9.2. The slurry was filtered and the clear, red filtrate (650 ml) was treated with a solution of 1 g oxalic acid dihydrate and 0.85 g sodium carbonate in 20 ml water. After stirring for 15 minutes, the solution was filtered through an S&S #589 paper, precoated with 1 g of filteraid. The resultant solution was heated to 50° C. and salted to 25% based on volume, with 187.5 g sodium acetate. Dye crystallized, but was redissolved by heating to about 65° C. Stirring and cooling during one hour to 25° C. gave crystalline precipitate. Filtration gave 38.4 g paste. Air drying over the weekend gave 32.8 g. This partially dried dye was slurried in 95% ethanol in a Soxhlet extractor cup and extracted with 95% ethanol for six hours. The residual slurry was filtered, washed once with 95% ethanol, and dried in a vacuum oven at 120° C. yielding 22.1 g red crystals. The dye 6.0 g, and charcoal 0.5 g were refluxed 15 minutes in 120 ml ethanol/water (2/1 v/v) and filtered hot through Whatman No. 1 filter paper. Crystals appeared within 30 minutes. The solution was left at room temperature overnight, swirled, and stored at 5° C. for four hours. The material was filtered and drained on a Buchner funnel, but not sucked dry. It was washed twice with ethanol and left to dry in a fume hood over a weekend. 4.2 g (70% recovery) of dark green crystals with a metallic sheen were obtained, mp. >335° C., having no alcohol contamination according to proton NMR. Thin layer chromatography on Analtech silica gel RPSF plate showed the dye to be quite pure with respect to other colored impurities and u.v. absorbing colorless impurities. It analyzed C 32.42, 32.07; H 4.51, 5.00; N 2.74, 2.55; S 13.38, 13.27; Na 6.50, 6.45%, whereas $C_{27}H_{27}N_2S_4O_{13}Na_3 \cdot 12H_2O$ requires C 31.82, H 5.24, N 2.75, S 12.59, Na 6.77%.

EXAMPLE 2

Preparation of 1,11-bis(3-sulfopropyl)-1,2,3,4,8,9,10,11-octahydro-6—(2,4-disulfophenyl)-dipyrido[3,2-b:2',3'-i]-xanthylium inner salt, trisodium salt. 5b (1). 3-N-(7-Hydroxy-1,2,3,4-tetrahydroquinolinyl)-propane sulfonic acid 2b. Into a 250 ml Erlenmeyer flask was weighed 14.9 g (0.1 mole) 1,2,3,4-tetrahydro-7-hydroxyquinoline. It was dissolved in 75 ml anhydrous methanol. Propane sulfone (25 g, 0.205 mole) melted in the bottle with a hot air gun, was then added, and the air in the flask was displaced with inert gas ($N_2$ or Argon). The flask was capped with a ground-glass stopper. The mixture was stirred at ambient temperature (it rose to 35° C.) with a magnetic stirrer for 48 hours. During this time white product crystallized. The slurry was filtered on a 4.25 cm Buchner funnel, and the cake was washed with methanol, giving a white paste (35 g) which dried in air to 15.5 g (57.2% of theoretical). A sample recrystallized from water (5 ml/g, 55% recovery) and air-dried, had mp. 243°–245° C. (decomp.), and analyzed C 53.27, H 6.43, N 5.29, S 12.01%, whereas $C_{12}H_{17}NO_4S$ requires C 53.12, H 6.32, N 5.16, S 11.82%.

(2). Condensation. A mixture of 17.31 g (50 mmol) of benzaldehyde-2,4-disulfonic acid, sodium salt and 27.13 g (100 mmol) of the sulfonic acid 2b was ground together in a mortar. The mixture became yellow and slightly sticky. It and 26 g of 30% (w/w) sulfuric acid contained in a 250 ml round bottom flask was placed in an oil bath at 110° C. A solution formed. At 20 min, solid was starting to form and an aliquot neutralized with sodium carbonate showed no starting tetrahydroquinoline on TLC (RPS-F, 9/1, water:methanol). At 30 min, 125 ml of ethanol was added and the mixture was heated under reflux for 0.5 hr. It was then allowed to cool to room temperature. The solid was collected, washed with ethanol and dried overnight in the vacuum oven to give 31.24 g (75%). This solid gained weight on standing in air.

(3). Ring closure. A solution of 31.24 g (37.4 mmol) of the above leuco acid in 160 ml of 90% (w/w) sulfuric acid (13.3 g of water made to 160 g with 96.6% sulfuric acid) was heated in an oil bath at 1350 (internal) for 2 hr. It was then allowed to cool slightly and poured onto 200 g of ice. The flask was rinsed with 200 ml of water to give a red solution.

(4). Oxidation and Purification. The solution was stirred and heated to 70°. During 5 min 19.07 g (35.8 mmol) of ferric sulfate (75%) was added. The reaction mixture was held at 70° for 0.5 hr. Then 110 g of calcium hydroxide was added in portions during 0.5 hr. to the vigorously stirred mixture. The temperature went as high as 85° and the pH was 0.7. Another 2 g of calcium hydroxide was added and the mixture was stirred overnight at room temperature. The pH was 1.6. The mixture was reheated to ca 70° and another 2 g of calcium hydroxide was added. During 3 hr. the pH rose to 2.28. The insoluble precipitate was filtered and the filter cake washed four times with 100 ml of warm water. The pH of the filtrate was adjusted to 9.3 by the addition of 18 g of sodium carbonate in portions. 0.5 g of oxalic acid and then 3 g of sodium carbonate was added to give a pH of 9.5. The suspension was heated at 70° for 0.5 hr. and filtered through a funnel precoated with 3 g of Celite washing three times with water to give about 1 l of filtrate. The filtrate was concentrated in vacuo at 70° to 159 g. To it was added 300 ml of ethanol and the mixture heated to boiling. It was filtered hot and then cooled in the refrigerator. The solid that crystallized out was collected, washed with ethanol and air-dried overnight to give 25.15 g, 63% of crude 5b. Recrystallization from 375 ml of 75% ethanol/water with 3 g of charcoal gave 20.4 g (61% recovery) of golden crystals. It had mp. >335° C.

TLC showed a small spot for a less polar dye (RPS-F plates with 8/2 or 7/3 water:methanol or silica gel plates with 10% water in acetonitrile), although according to NMR any impurity was probably less than 1%. Likewise, there was no alcohol contamination. It analyzed C 35.93, 35.87; H 4.99, 5.07; N 2.32, 2.40; S 12.71, 12.71; Na 6.24, 6.56%, whereas $C_{31}H_{31}N_2S_4O_{13}Na_3 \cdot 12H_2O$ requires C 35.36, H 5.26, N 2.66, S 12.18, Na 6.55%

EXAMPLE 3

Spectral and Oscillator Properties of 5a and 5b 5a sodium salt. M 1000.95; $\epsilon_{488}=0.269\times10^5$; $\epsilon_{510.6}=0.499\times10^5$; $\epsilon_{531}$ (the absorption maximum)$=1.035\times10^5$; $\epsilon_{532}=1.034\times10^5$. All measurements are in water.

5b sodium salt. M 1053.02; $\epsilon_{488}=0.066\times10^5$; $\epsilon_{510.6}=0.185\times10^5$; $\epsilon_{532}=0.416\times10^5$; $\epsilon_{569}$ (the absorption maximum)$=1.302\times10^5$; $\epsilon_{578.2}=0.968\times10^5$. All measurements are in water. The comparisons of the properties of 5a and 5b with other water soluble dyes provided by the present invention are set forth in the table of Example 8.

EXAMPLE 4

Preparation of Laser Dye 8c (1). 2-N-(6-Hydroxyindolinyl)ethanesulfonic acid 6c. A mixture of 16.74 g (122 mmol) of 6-hydroxyindoline, 31.7 g (150 mmol) of 2-bromoethanesulfonic acid sodium salt, 12.6 g (150 mmol) of sodium bicarbonate and 80 ml of water was stirred and heated under reflux under nitrogen for 4.5 hr.

The reaction mixture was allowed to cool to room temperature and then acidified with 13 ml of concentrated hydrochloric acid. It was seeded and cooled overnight in the refrigerator. The product was collected and rinsed with a little ice water. After drying overnight in the hood there was 27.25 g (91% of theory for unhydrated material), mp 272°–275° dec. It appears to be slightly hygroscopic. A sample for analysis was obtained by recrystallization from aqueous methanol as off-white plates, mp 285°–289° dec.

Anal. Calcd for $C_{10}H_{13}NO_4S$:C, 49.37; H, 5.38; N, 5.76. Found: C, 49.64; H, 5.39; N, 5.74.

(2). Leuco Acid 7c. A mixture of 21.41 g (88 mmol) of the ethanesulfonic acid, 6c, and 13.84 g (40 mmol) of benzaldehyde-2,4-disulfonic acid sodium salt was ground together in a mortar. This mixture was added to 24.6 g of 32% (w/w) sulfuric acid stirred in an oil bath at 94°–97°. At first a cake formed which was broken up. It later dissolved. Heating was continued for 3 hr. Then 100 ml of methanol was added and the mixture heated under reflux for 20 min. A solid formed. After cooling overnight in the refrigerator this was collected and washed with methanol to give 27.56 g (89%) of leuco acid 7c after drying.

(3). Laser dye 8c. a). To 30 g of 90% sulfuric acid (prepared from 2 g of water diluted to 30 g with 96.6% sulfuric acid) was added 5.6 g (7.2 mmol) of leuco acid, 7c. This mixture was stirred under nitrogen and heated at 100° for 3 hr. It was poured onto 50 g of ice in a 400 ml beaker. The flask was rinsed with water and then ice was added to give 100 ml of red solution. At ca. 5° a solution of 0.36 g of sodium nitrite in 5 ml of water was added dropwise during 10 min. Some nitrous fumes were given off. After 20 min 0.2 g of sodium nitrite in 2 ml of water was added. The reaction mixture was stirred for 0.5 hr. To the stirred reaction mixture was added 20 g of calcium hydroxide in portions during 30 min. The temperature was mostly in the range 65°–70°. The pH after another 15 min was 0.4. A further 1 g of calcium hydroxide was added, and the mixture was stirred overnight. In the morning the pH was 11. The pH was adjusted to 6.7 by the addition of 1 ml of acetic acid. The precipitated calcium sulfate was filtered off and washed with 100 ml of warm water in 3 portions to remove most of the dye. Spectroscopy indicated 5 mmol (70%) of dye present. The filtrate was concentrated in vacuo at 70° to leave 7.49 g of purple tar. This was dissolved in 20 ml of warm water. The solution was diluted with 180 ml of ethanol, heated to boiling and filtered. On cooling an oil separated which solidified on scratching. The product was collected and dried to give 2.79 g of dark solid with an apparent ε of 119,500. This was recrystallized from 200 ml of 85% aqueous ethanol to give 2.18 g of purple needles, mp >360°; $\lambda_{max}$ 555 nm.

Anal. Calcd for $C_{27}H_{23}N_2Na_3O_{13}S_5 \cdot 3H_2O$ (MW 834.77): C, 38.85; H, 3.50; N, 3.36; Na, 8.26; S, 15.36; $H_2O$, 6.47; Found: C, 38.71; H, 3.61; N, 3.15; Na, 8.18; S, 15.31; $H_2O$, (Karl Fischer), 6.65.

b). To 60 g of 90% (w/w) sulfuric acid from 4 g of water made up to 60 g with 96.6% sulfuric acid contained in a 100 ml round bottom flask was added 12 g (15.4 mmol) of the above leuco acid, 7c. This mixture was stirred under nitrogen in an oil bath at 95°–110° (internal temperature) for 2 hr. It was then poured onto 100 g of ice, and the flask was rinsed with water to give 250 ml of red solution. The solution was warmed on a hot plate and treated with 8 g (15.1 mmol) of 75% ferric sulfate. After 20 min at ca. 400 addition of 42 g of calcium hydroxide was commenced. This operation took 20 min and the temperature rose to 70°. The mixture was stirred overnight without heating. In the morning the pH was 1.1 and 3 g of sodium carbonate was added. The pH was 3.5. Then 3 g more calcium hydroxide was added to bring the pH to 11.6. The precipitated calcium sulfate was filtered off and washed with 200 ml of warm water in four portions to remove most of the occluded dye. The pH of the filtrate was adjusted to 3.3 by the addition of 4 ml of acetic acid. The visible spectrum of an aliquot of the filtrate indicated about 10 mmol of dye present. The filtrate was concentrated to dryness on the rotary evaporator at 70° to leave 16.64 g of dark residue. This was dissolved in 60 ml of water and transferred to a 1 l Erlenmeyer. The solution was diluted to 600 ml with 95% ethanol, heated to boiling and filtered. The filtrate was seeded and cooled overnight in the refrigerator to precipitate 6.49 g of crude 8c after drying. It had an apparent ε of 105,000; i.e. 84% pure for a yield of 48%.

Recrystallization of 25.35 g of similar material by dissolution in 150 ml of water, dilution to 1.4 l with 95% ethanol and treatment with 3 g of charcoal after heating to boiling gave 21.4 g of 8c after drying in a vacuum oven at 80°.

EXAMPLE 5

Preparation of laser dye 8b (1). 2-N-(7-Hydroxy-1,2,3,4-tetrahydroquinolinyl) ethanesulfonic acid 6b. A mixture of 44.76 g (0.3 mol) of 7-hydroxy-1,2,3,4 tetrahydroquinoline, 1b, 76 g (0.36 mol) of the sodium salt of 2-bromoethanesulfonic acid, 30.24 g (0.36 mol) of sodium bicarbonate and 200 ml of water was stirred and heated under reflux for 4 hr. The reaction mixture was allowed to cool, acidified with 32 ml of concentrated hydrochloric acid, seeded and cooled overnight in the refrigerator. The solid was collected, rinsed with water and dried to give 56.45 g (73%) of crude product, mp 283°–287° dec. Crystallization from 1 l of water with 6 g of charcoal gave 44.22 g (57%) of product, mp 294°–299° dec. An analytical sample prepared by recrystallization from water was obtained as pale lavender prisms, mp 298°–304° dec.

Anal. Calcd for $C_{11}H_{15}NO_4$: C, 51.35; H, 5.88; N, 5.44. Found: C, 51.46; H, 5.99; N, 5.56.

(2). Leuco Acid 7b. A mixture of 67.6 g (263 mmol) of the ethanesulfonic acid, 6b, and 40 g (116 mmol) of benzaldehyde-2,4-disulfonic acid sodium salt was added to 75 g of 30% (w/w) sulfuric acid stirred in an oil bath at 110°. Heating was continued for 2.5 hr. After 20 min a precipitate had started to form. The mixture was diluted with 400 ml of methanol and heated under reflux for 90 min. A thick paste formed. After cooling overnight in the refrigerator this was collected and washed with methanol to give 94.5 g (98%) of crude leuco acid after drying.

(3). Ring closure and oxidation. To 200 g of 90% (w/w) sulfuric acid from 13.7 g of water made up to 60 g with 96.6% sulfuric acid contained in a 250 ml round bottom flask was added 40 g (48 mmol) of the above leuco acid, 7b. This mixture was stirred under nitrogen in an oil bath at 120° (internal temperature) for 2 hr and allowed to cool overnight. It was then poured onto 400 g of ice, and the flask was rinsed with water to give 800 ml of red solution. This solution was warmed on a hot plate and treated with 25.6 g (48 mmol) of 75% ferric sulfate. After 20 min at ca. 40° addition of 149 g of calcium hydroxide was commenced. This operation took 80 min and the temperature rose to 70°. After the reaction mixture had stirred for 2 hr, the pH was 1.6. An additional 1 g of calcium hydroxide and 10 g of sodium carbonate was added and the mixture was stirred overnight at room temperature. The pH was 8.5. The calcium sulfate was filtered off and washed with 7×100 ml of warm water. The filtrate was concentrated in vacuo to leave 57.3 g of dark residue. This residue was transferred with 200 ml of water to a 4 l Erlenmeyer flask. The solution was diluted to 2.5 l with boiling 95% ethanol, filtered, seeded and cooled in the refrigerator over the weekend. The precipitated product was collected, rinsed with ethanol and dried in vacuo at 70° to give 25.26 g of brown-gold solid [$\lambda_{max}$ 563 nm, apparent $\epsilon$ of 103,600]. This solid was recrystallized from 1.8 l of 85% ethanol with 5 g of charcoal to give 16.2 g of product 8b. For analysis a sample was again recrystallized from 85% aqueous ethanol.

EXAMPLE 6

Preparation of laser dye 5d, 9-[2,4-disulphophenyl]-3,6-bis(3-sulfopropylamino)-4,5-dimethylxanthylium inner salt, trisodium salt.

3-N-[2'-methyl-3'-hydroxyphenyl] aminopropanesulfonic acid 2d. To a solution of 20.1 g (0.164 mol) of 1,3-propanesultone in 200 ml of toluene heated to reflux was added 14.78 g (0.12 mol) 3-amino-o-cresol; the mixture was stirred and heated for 18 hr. It was then allowed to cool to room temperature. The solid was collected and rinsed with toluene to give 28.55 g of (97%) of crude product. Recrystallization from 200 ml of 1N hydrochloric acid with charcoal gave 18.39 g (63%) of product, mp 280°–282° dec. An analytical sample prepared by recrystallization from 3N hydrochloric acid had mp 283°–5° dec.

Anal. Calcd for $C_{10}H_{15}NO_4S$: C, 48.96; H, 6.16; N, 5.71. Found: C, 48.72; H, 6.22; N, 6.25.

Leuco acid, ring closure and oxidation

A mixture of 3.68 g (15 mmole) of the aminopropanesulfonic acid 2d, 2.42 g (7 mmole) of benzaldehyde-2,4-disulfonic acid sodium salt and 15 ml of 30% (w/w) sulfuric acid was stirred and heated under reflux for 24 hr. It was cooled, diluted to 50 ml with water and neutralized to pH 3.9 with 4.4 g of calcium hydroxide. The calcium sulfate was filtered off washing with 2×10 ml of water. The filtrate was concentrated in vacuo to 6 g of red tar. This residue was heated with 30 ml of 90% sulfuric acid at 125°–130° for 2 hr. The solution was poured onto 50 g of ice and the flask rinsed with enough water to make 100 ml of solution. To the solution was added 0.6 g of sodium nitrite. No dye formed. The solution was heated to 70° and 3.7 g (7 mmole) of ferric sulfate was added during 10 min. After 20 min the visible spectrum of an aliquot indicated that 2.35 mmole (33%) of dye was present. The solution was allowed to stand over the week end at room temperature. A small amount of colorless solid was filtered off. The filtrate was stirred and treated with 23.5 g of calcium hydroxide at 70°–90°. After 2 hr at 70° the pH was 11.5. The solid was collected and washed with 4×25 ml of warm water. The filtrate was treated with 0.5 g of oxalic acid and 0.4 g of sodium carbonate to give a pH of 8. It was refiltered through Celite. The filtrate was treated with 0.5 ml of acetic acid and concentrated in vacuo to give 6.77 g of purple tar. This was scratched and collected with ethanol to give 6.4 g of dark solid. This solid was dissolved in 6 ml of water. To this solution was added 12 ml of ethanol and it was allowed to stand overnight. A tarry mass formed. It did not filter well. The sticky solid (4.3 g) was recrystallized from 30 ml of 75% ethanol to give 1.22 g of sticky dark solid (estimated by absorption spectroscopy to be 54% pure). A further recrystallization from 20 ml 75% aq. ethanol gave 0.59 g of solid estimated to be 72% pure.

For analysis this material was combined with that from two similar experiments and recrystallized twice more from 75% ethanol, once with charcoal, to give dark prisms.

Anal. Calcd. for $C_{27}H_{27}N_2Na_3O_{13}S_4 \cdot 9H_2O$ (m 946.88): C, 34.25; H, 4.79, N, 2.96. Found: C, 34.36; H, 4.81; N, 2.95.

EXAMPLE 7

Preparation of Pyronin Dye ("PQE") and Oxazine Dye ("OQE")

(1) Pyronin Dye PQE (a). Condensation with Formaldehyde 2-N-(7-Hydroxy-1,2,3,4-tetrahydroquinolinyl)ethanesulfonic acid 6b (9.2 g-0.035 mole) was pasted in 25 ml deionized water. The slurry was neutralized by cautious addition of 1.9 g sodium carbonate and then with good stirring treated dropwise with 1.42 g (1.73 ml) of 37% w/w formaldehyde solution. It became a thick white paste, even when diluted to 75 ml vol. (pH 6.0). Hydrochloric acid, 4 ml-37%, was added to pH<1 and the reaction mix was heated to 75° C. After 20 min. at this temperature, with further dilution to 100 ml. volume, it was cooled in an ice bath to 10° C. and filtered. The cake was washed with 20 ml deionized water and sucked fairly dry giving 17.4 g paste which dried in vacuum oven at 60°–80° C. to 10.8 g colorless solid in 1 hour.

(b). Ring Closure—Pyronization

The product from formaldehyde condensation was charged to a 50 ml round bottom flask and treated with 1.3 g. water and 20 g 96.4% sulfuric acid (i.e. 90.5% sulfuric acid). Heating with stirring gave a yellow solution.

Heating was continued to 135°–145° C. and the temperature was held in this range for 2 hours during which the color of the solution changed to deep orange, with reddish tinge. After cooling overnight the solution was poured onto 40 g ice and the flask rinsed with some of the diluted reaction plus some water to 100 ml volume. A slightly colored precipitate was present which was filtered on a sintered glass funnel and washed several times with deionized water (50 ml total) giving 19.8 g of paste. This was slurried in 50 ml 95% ethanol, and treated dropwise with good stirring with a solution of 1 g $NaNO_2$ in 5 ml water. The pale pink colored precipitate gradually converted to dark red crystals and the slurry thinned somewhat. Dilution to 100 ml volume with 95% ethanol and filtration followed by washing of the cake with 20 ml 95° ethanol gave 10.5 g paste which dried to 6.8 g (71% of theoretical). TLC on silica gel with methanol showed a large red spot with a minor colorless spot which led, and later turned red upon drying.

(2) Oxazine Dye OQE 2-N-(7-Hydroxy-1,2,3,4-tetrahydroquinolinyl)ethanesulfonic acid 6b (5.15 g -0.02 mole) was dissolved in 20 ml deionized water with 1.06 g sodium carbonate. A solution of sodium nitrite (0.7 g; 0.01 mole) in 2 ml deionized water was added. This mixture was slowly poured into a stirring mixture of 4 ml 37% hydrochloric acid and ice sufficient to maintain temperature at 0° C. The nitrous acid was absorbed rapidly. The solution was heated to 75°–80° C. and held for 1 hour. To the cooled blue solution was added 0.5 g Darco and the solution was stirred 5 minutes. Clarification, using 1 g Celite, was performed on Buchner funnel. Addition of isopropanol 450 ml was found to precipitate the dye, however, together with impurities present. The precipitate was separated after standing overnight, by decantation, and then dissolved in water (150 ml volume). This solution was loaded onto a column containing 200 g silica gel (70–230 mesh) and eluted with deionized water. The first fractions were yellowish-brown, then green. Later, fractions were bright blue and relatively free of impurities. These fractions were combined and evaporated in the Rotavapor and finally in an evaporating dish to dryness giving 0.5 g product. A sample of 200 mg was recrystallized from 80–85% ethanol.

(3). The presence of the pyronin and oxazine dyes were confirmed using proton magnetic resonance spectroscopy.

EXAMPLE 8

Comparisons of the spectral properties and oscillator tuning curves for the various dyes are as follows:

TABLE 1

Spectral Properties and Oscillator Tuning Curves for Dyes in Water

| Dye | $\lambda_{max}$ (nm) | $\epsilon_{max}$ (× $10^{-5}$) | Pump* | $\epsilon_{pump}$ (× $10^{-5}$) | Molarity (× $10^{-3}$) | Tuning Curve $\lambda_{max}$ (nm) | Tuning Curve FWHM (nm) |
|---|---|---|---|---|---|---|---|
| 8C | 556 | 1.168 | G | 0.339 | 0.98 | 613 | 590–637 |
| 8C | 556 | 1.168 | Y | 0.196 | 1.70 | 622 | 594–643 |
| 8B | 564 | 1.194 | G | 0.207 | 1.61 | 605 | 595–638 |
| 8B | 564 | 1.194 | Y | 0.647 | 0.52 | 632 | 605–648 |
| 5D | 546 | 1.118 | G | 0.374 | 0.89 | 617 | 595–618 |
| 5D | 546 | 1.118 | Y | 0.048 | 6.94 | No laser action | |
| 5A | 531 | 1.035 | G | 0.499 | 0.67 | 568 | 560–592 |
| 5B | 569 | 1.302 | G | 0.185 | 1.80 | 639 | 616–655 |
| 5B | 569 | 1.302 | Y | 0.968 | 0.34 | 607 | 598–643 |

*G pump wavelength 510.6 nm, Y pump wavelength 578.2 nm.

What is claimed is:

1. A composition of matter having the formula I:

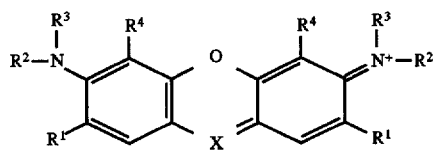 (I)

wherein:

$R^1$ and $R^4$ are alkyl of 1 to 4 carbon atoms or hydrogen; or $R^1$-$R^2$ or $R^2$-$R^4$ form part of aliphatic heterocyclic rings;

$R^2$ is hydrogen or joined with $R^1$ or $R^4$ as described above;

$R^3$ is —$(CH_2)_m$—$SO_3^-$; where m is 1 to 6; and

X is CH.

2. The composition of claim 1 wherein m is 2 and $R^1$-$R^2$ is —$(CH_2)_3$—.

3. A composition of matter having the formula I:

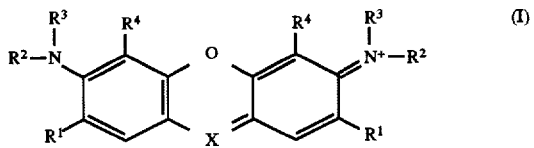 (I)

wherein:

$R^1$ and $R^4$ are alkyl of 1 to 4 carbon atoms or hydrogen; or $R^1$-$R^2$ or $R^2$-$R^4$ form part of aliphatic heterocyclic rings;

$R^2$ is hydrogen or joined with $R^1$ or $R^4$ as described above;

$R^3$ is —$(CH_2)_m$—$SO_3^-$; where m is 1 to 6;

X is nitrogen.

4. The composition of claim 3 wherein m is 2 and $R^1$-$R^2$ is —$(CH_2)_3$—.

5. A composition of matter having the formula I:

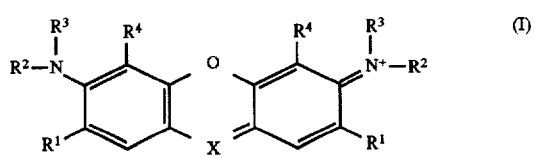 (I)

wherein $R^1$-$R^2$ are joined in a ring of the form —$(CH_2)_{(2\ or\ 3)}$—;
$R^4$=H;
$R^3$ is —$(CH_2)_m$—$SO_3^-$, where m is 1 to 6;
X is N, CH or

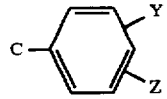

wherein

Y is —$SO_3^-$ at position 2 of the ring; and
Z is —$SO_3^-$ at position 4 of the ring.

* * * * *